(12) United States Patent
Awazu et al.

(10) Patent No.: US 10,166,086 B2
(45) Date of Patent: Jan. 1, 2019

(54) DENTAL THERAPY APPARATUS

(75) Inventors: Kunio Awazu, Suita (JP); Katsunori Ishii, Suita (JP); Naota Akikusa, Hamamatsu (JP); Tadataka Edamura, Hamamatsu (JP); Hirofumi Kan, Hamamatsu (JP)

(73) Assignees: OSAKA UNIVERSITY, Suita-shi, Osaka (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 790 days.

(21) Appl. No.: 14/110,837

(22) PCT Filed: May 17, 2012

(86) PCT No.: PCT/JP2012/062653
§ 371 (c)(1),
(2), (4) Date: Oct. 9, 2013

(87) PCT Pub. No.: WO2012/165162
PCT Pub. Date: Dec. 6, 2012

(65) Prior Publication Data
US 2014/0030671 A1 Jan. 30, 2014

(30) Foreign Application Priority Data
Jun. 1, 2011 (JP) ................. 2011-123662

(51) Int. Cl.
A61C 1/00 (2006.01)
A61C 3/02 (2006.01)

(52) U.S. Cl.
CPC .......... *A61C 1/0046* (2013.01); *A61C 1/0015* (2013.01); *A61C 3/02* (2013.01)

(58) Field of Classification Search
CPC .. A61C 1/0046; C09K 19/3804; B82Y 20/00; F01C 21/02; A61N 5/0603; A61B 18/26
(Continued)

(56) References Cited

U.S. PATENT DOCUMENTS 5,403,306 A 4/1995 Edwards et al.
5,720,894 A * 2/1998 Neev ...................... A61B 18/20
216/65
(Continued)

FOREIGN PATENT DOCUMENTS

CN 1182573 5/1998
JP H10-33557 A * 2/1988 ........... A61C 1/0046
(Continued)

OTHER PUBLICATIONS

Masayuki Saiki et al., "Selective treatment technique of carious dentin using a pulsed lase with 6 μm wavelength range," Research document of The Institute of Electrical Engineers of Japan, Research on optical/quantum devices Biomedical applications, IEE Japan, OQD-10-25, Mar. 24, 2010, pp. 31-34, including partial English translation.
(Continued)

*Primary Examiner* — Boniface N Nganga
(74) *Attorney, Agent, or Firm* — Drinker Biddle & Reath LLP

(57) ABSTRACT

A dental therapy apparatus which enables a dental therapy more surely and less invasively is provided. A dental therapy apparatus (10A) comprises a laser light source (11) emitting laser light (L) having a wavelength within a wavelength region of 5.7 to 6.6 μm; a controller (12) pulse-driving the laser light source and controlling at least one of pulse width and repetition frequency of pulsed laser light emitted from the laser light source; and an irradiation optical system for irradiating a tooth (20) including a carious part (21) with the light emitted from the laser light source. In this dental therapy apparatus, the controller controls at least one of the pulse width and repetition frequency of the pulsed light, so as to selectively cut the carious part (21).

1 Claim, 7 Drawing Sheets

(58) Field of Classification Search
USPC ..... 433/29, 215; 252/299.01; 372/45.01, 32; 417/420; 219/121.69
See application file for complete search history.

(56) References Cited

U.S. PATENT DOCUMENTS

| | | | | |
|---|---|---|---|---|
| 6,083,218 | A * | 7/2000 | Chou | A61C 1/0046 433/215 |
| 6,270,324 | B1 * | 8/2001 | Sullivan | F01C 21/02 417/420 |
| RE37,585 | E * | 3/2002 | Mourou | A61B 18/20 219/121.69 |
| 7,144,247 | B2 * | 12/2006 | Black | A61N 5/0603 433/29 |
| 7,167,622 | B2 | 1/2007 | Temelkuran et al. | |
| 7,231,122 | B2 | 6/2007 | Weisberg et al. | |
| 7,310,466 | B2 | 12/2007 | Fink et al. | |
| 7,331,954 | B2 | 2/2008 | Temelkuran et al. | |
| 7,349,589 | B2 | 3/2008 | Temelkuran et al. | |
| 7,817,687 | B2 * | 10/2010 | Rizoiu | A61B 18/26 372/25 |
| 7,991,258 | B2 | 8/2011 | Temelkuran et al. | |
| 8,280,212 | B2 | 10/2012 | Goell et al. | |
| 8,320,725 | B2 | 11/2012 | Temelkuran et al. | |
| 8,761,561 | B2 | 6/2014 | Temelkuran et al. | |
| 2004/0161009 | A1 * | 8/2004 | Edamura | B82Y 20/00 372/45.01 |
| 2006/0195072 | A1 | 8/2006 | Miller | |
| 2007/0122096 | A1 | 5/2007 | Temelkuran et al. | |
| 2008/0086118 | A1 * | 4/2008 | Lai | A61B 18/20 606/11 |
| 2009/0028197 | A1 * | 1/2009 | Arnone | B82Y 20/00 372/32 |
| 2011/0207075 | A1 | 8/2011 | Altshuler et al. | |
| 2012/0321262 | A1 | 12/2012 | Goell et al. | |
| 2013/0123766 | A1 | 5/2013 | Temelkuran et al. | |
| 2014/0005646 | A1 | 1/2014 | Temelkuran et al. | |

FOREIGN PATENT DOCUMENTS

| | | | |
|---|---|---|---|
| JP | H05-309101 | 11/1993 | |
| JP | H10-33557 A | 2/1998 | |
| JP | 2004-261288 A | 9/2004 | |
| JP | 2004261288 A * | 9/2004 | ............ A61B 18/20 |
| JP | 2007-532955 | 11/2007 | |
| JP | 2008-509755 A | 4/2008 | |
| JP | 2008-526276 A | 7/2008 | |
| JP | 2008-197080 | 8/2008 | |
| JP | 2009-526591 | 7/2009 | |
| JP | 2010-042182 | 2/2010 | |
| JP | 2010-068880 | 4/2010 | |

OTHER PUBLICATIONS

Masayuki Saiki et al., "Hacho 6.02μm no Nano Byo Pulse Laser ni yoru Dakkai Zogeshitsu no Sentakuteki Setsujo (Selective Removal of Demineralized Dentin Using a Nanosecond Pulsed Laser with the Wavelength of 6.02μm)," Journal of Japanese Society for Laser Dentistry, Apr. 2011, pp. 16-20, vol. 22, No. 1, including partial English translation.

Katsunori Ishii et al., "Development of Selective Laser Treatment Techniques using Mid-infrared Tunable Nanosecond Pulsed Laser," IEEE Engineering in Medicine and Biology Society, 32nd Annual International Conference, 2010, pp. 1614-1617.

* cited by examiner

Fig.3

Fig.4
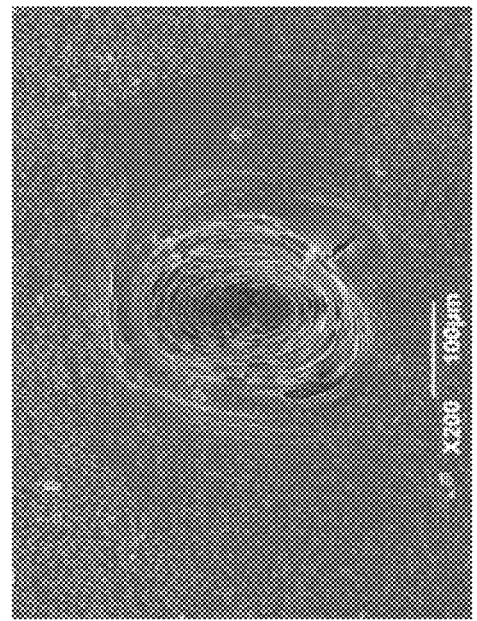
(b)
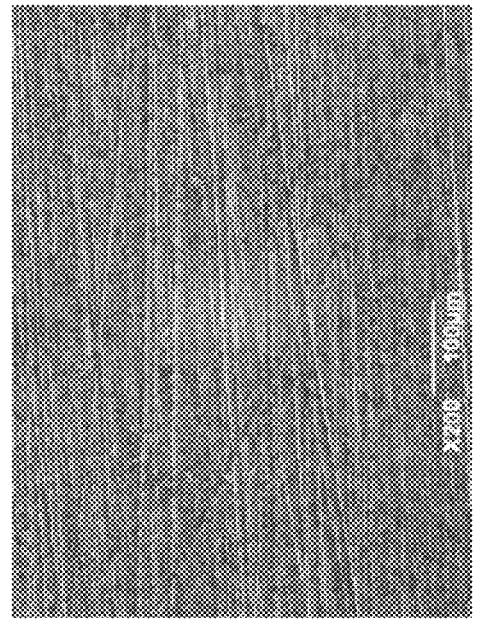
(a)

Fig.6
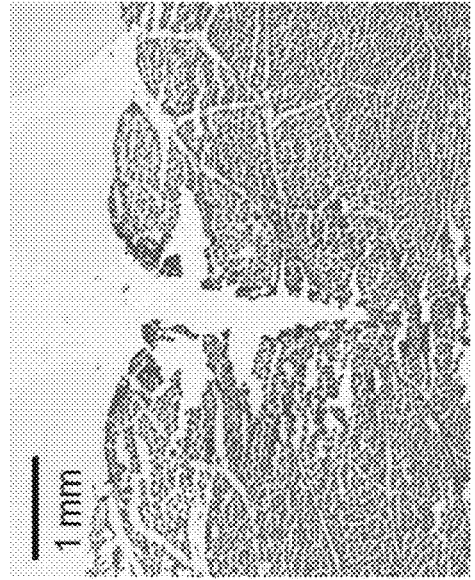

DENTAL THERAPY APPARATUS

TECHNICAL FIELD

The present invention relates to a dental therapy apparatus.

BACKGROUND ART

Carious teeth, so-called dental caries, have recently been treated with rotary cutting devices typified by air turbines or Er:YAG laser light having a wavelength of 2.94 μm. Such techniques cannot separate sound and carious parts from each other. Therefore, the treatment for dental caries tends to depend on skills of dentists. Hence, minimally invasive therapeutic techniques which can selectively process carious parts have been in demand. As one of such techniques, those of Non Patent Literatures 1 and 2 utilizing a mid-infrared wavelength-variable laser of difference-frequency generation (DFG) type (hereinafter referred to as DFG laser) have been known. The difference-frequency generation is a method which makes two kinds of wavelengths $\lambda_1$, $\lambda_2$ incident on a nonlinear optical crystal and satisfies a phase-matching condition, so as to generate light having a wavelength $\lambda_3$. The DFG laser of Non Patent Literature 1 employs $AgGaS_2$ (silver gallium sulfide) as a nonlinear optical crystal, and an Nd:YAG laser (wavelength $\lambda_1$: 1.064 μm) and a Cr:forsterite laser (wavelength $\lambda_2$: 1.15 to 1.36 μm) as DFG pumping light and signal light, respectively. This is the same in Non Patent Literature 2.

CITATION LIST

Non Patent Literature

Non Patent Literature 1: SAIKI Masayuki and 5 others, "Selective treatment technique of carious dentin using a pulsed laser with 6 μm wavelength range," The Papers of Technical Meeting on Biomedical Applications of Optical and Quantum Devices, The Institute of Electrical Engineers of Japan, OQD-10-025 (2010), pp. 31-34. Non Patent Literature 2: SAIKI Masayuki, ISHII Katsunori, YOSHIKAWA Kazushi, YASUO Kenzo, YAMAMOTO Kazuyo, and AWAZU Kunio, "Selective Removal of Demineralized Dentin Using a Nanosecond Pulsed Laser with the Wavelength of 6.02 μm," Journal of Japanese Society for Laser Dentistry, 22 (2011), pp. 16-20.

SUMMARY OF INVENTION

Technical Problem

In the technique of Non Patent Literature 1, the laser light is emitted under driving conditions with a pulse width of 5 ns and a repetition frequency of 10 Hz, which facilitates the cutting of carious parts at a very high cutting speed. This, on the other hand, may damage intraoral soft tissues and the like.

It is therefore an object of the present invention to provide a dental therapy apparatus which enables a dental therapy more surely and less invasively.

Solution to Problem

The dental therapy apparatus in accordance with one aspect of the present invention comprises a laser light source emitting laser light having a wavelength within a wavelength region of 5.7 to 6.6 μm; a controller pulse-driving the laser light source and controlling at least one of pulse width and repetition frequency of pulsed laser light emitted from the laser light source; and an irradiation optical system for irradiating a tooth including a carious part with the light emitted from the laser light source. In this dental therapy apparatus, the controller controls at least one of the pulse width and repetition frequency of the pulsed laser light, so as to selectively cut the carious part.

This structure uses a laser light source which emits laser light having a wavelength within the wavelength region of 5.7 to 6.6 μm and thus can selectively cut a carious part while less affecting sound parts, for example. Further, the controller pulse-drives the laser light source and controls at least one of the pulse width and repetition frequency of the pulsed laser light. This control can change cutting conditions (e.g., cutting speed), whereby the carious part can be cut further selectively. As a result, dental therapies can be performed more surely.

The controller may switch the control of the laser light source between a first mode of driving the laser light source at a pulse width shorter than a thermal relaxation time of an area irradiated with the pulsed laser light and a repetition frequency lower than that corresponding to the thermal relaxation time and a second mode of driving the laser light source at a pulse width longer than the thermal relaxation time and a repetition frequency higher than that corresponding to the thermal relaxation time.

Driving the laser light source in the first mode performs cutting with depressed thermal actions. Driving the laser light source in the second mode, on the other hand, makes it easier for heat to diffuse to the outside of the area irradiated with the pulsed laser light emitted from the laser light source. For example, an intraoral soft tissue such as a gum may be ablated when irradiated with laser light. Bleeding occurs in this case, but the soft tissue can coagulate when the surroundings of the irradiated area attain a fixed temperature or higher due to the thermal diffusion, thereby yielding a hemostatic effect. Therefore, even when a soft tissue about a carious part is damaged during cutting the carious part in the first mode, for example, switching to the second mode can stop the soft tissue from bleeding.

The laser light source may be a quantum cascade laser. Utilizing the quantum cascade laser can make the dental therapy apparatus smaller.

Advantageous Effects of Invention

The present invention can provide a dental therapy apparatus which enables a dental therapy more surely and less invasively.

BRIEF DESCRIPTION OF DRAWINGS

Figure 3:
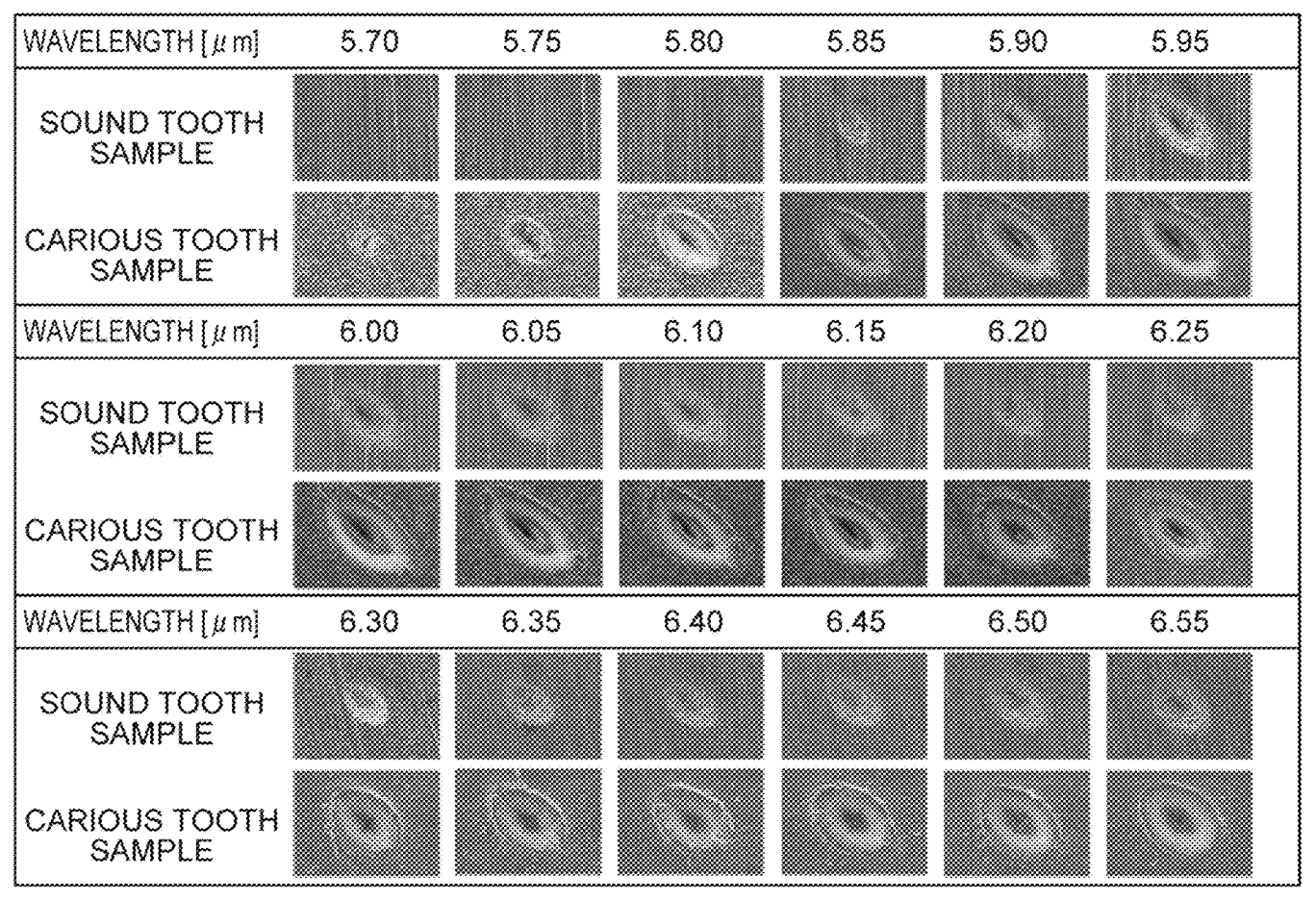

FIG. 3 is a chart illustrating how sound and carious tooth samples are cut at wavelengths in increments of 0.05 μm within the wavelength region of 5.70 to 6.55 μm;

FIG. 4(a) is a picture illustrating an irradiation mark of a sound tooth sample, while FIG. 4(b) is a picture illustrating an irradiation mark of a carious tooth sample;

FIGS. 6(a) and 6(b) are pictures illustrating cross sections of irradiation marks in samples irradiated with laser light at wavelengths of 5.7 μm and 10.6 μm, respectively.

DESCRIPTION OF EMBODIMENTS

Figure 1:
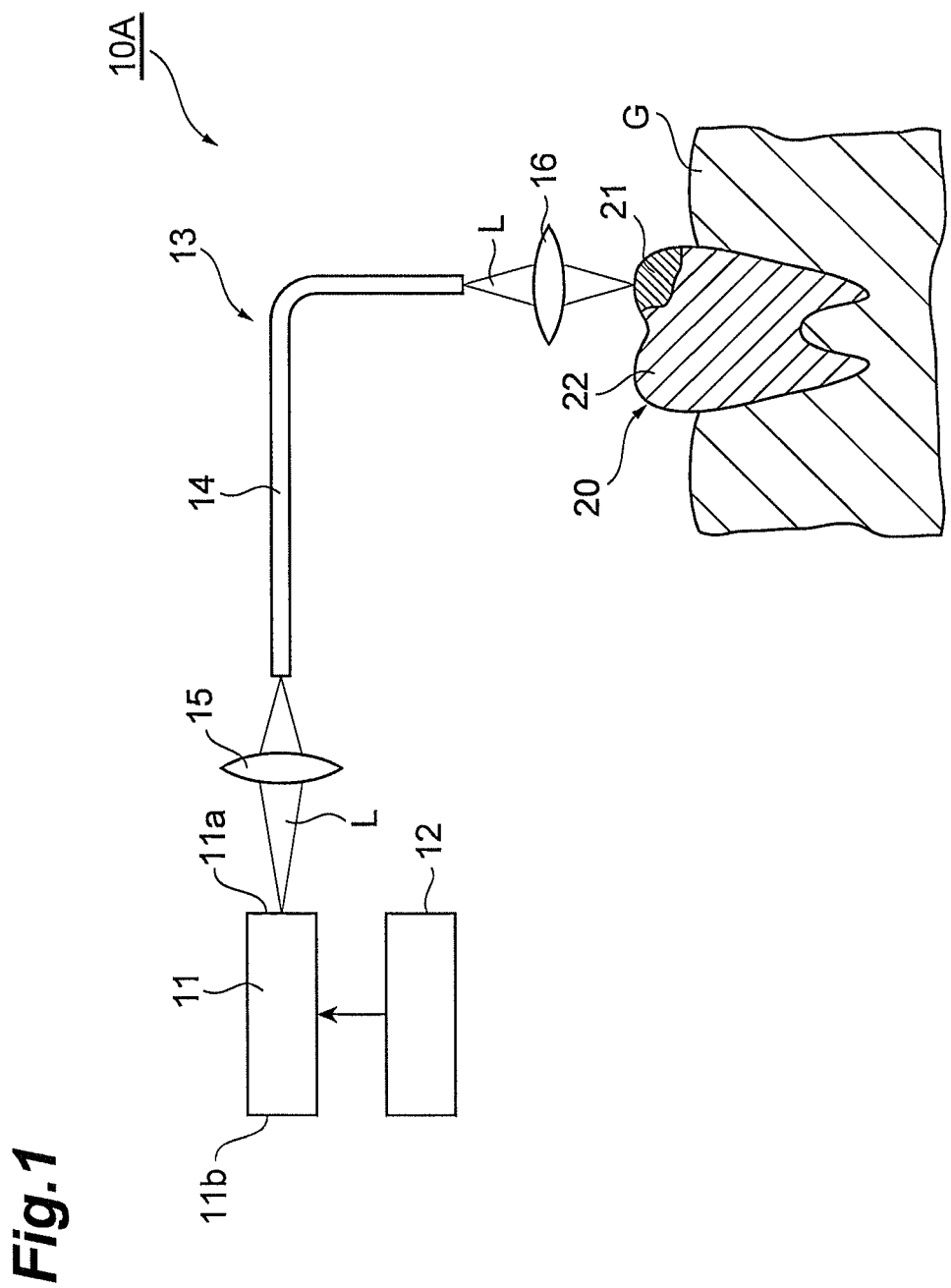
FIG. 1 is a schematic view illustrating a general structure of an example of dental therapy apparatus in accordance with an embodiment.

In the following, embodiments of the present invention will be explained in detail with reference to the drawings. In the drawings, the same constituents will be referred to with the same signs while omitting their overlapping descriptions. Ratios of dimensions in the drawings do not always coincide with those explained.

FIG. 1 is a schematic view illustrating a general structure of an example of dental therapy apparatus in accordance with one embodiment. FIG. 1 also schematically illustrates a carious tooth 20 to be treated with a dental therapy apparatus 10A. The carious tooth 20, which is a so-called dental caries, is a tooth having a carious part 21.

The dental therapy apparatus 10A has a laser light source 11 that emits laser light, a controller 12 that controls the driving of the laser light source 11, and an irradiation optical system 13 fort irradiating the carious tooth 20 as an object to be treated with the laser light L emitted from the laser light source 11. FIG. 1 illustrates only a main part of the dental therapy apparatus 10A. The dental therapy apparatus 10A may be a tooth processing apparatus for cutting the carious part 21.

The laser light source 11 is a quantum cascade laser which emits laser light having a wavelength within the wavelength region of 5.7 to 6.6 μm. The quantum cascade laser is a monopolar type optical waveguide semiconductor laser device which generates light by utilizing intersubband electronic transitions in a semiconductor quantum well structure. The laser light source 11 as a quantum cascade laser comprises a semiconductor substrate and an active layer formed on the semiconductor substrate. The laser light source 11 has front and rear end faces 11a, 11b which oppose each other and construct an optical resonator. The resonator structure of the laser light source (the front and rear end faces 11a, 11b) can be formed by cleaving both end faces. The structure and action of the quantum cascade laser have bee known (see, for example, Japanese Patent Application Laid-Open Nos. 2004-247492, 2005-039045, and 2008-177366) and will not be explained in more detail.

The controller 12 applies a voltage to the laser light source 11, thereby pulse-driving the latter. In this case, the laser light emitted from the laser light source 11 is pulsed laser light L (hereinafter simply referred to as pulse laser light L). By changing the state of voltage application to the laser light source 11, the controller 12 can control the pulse width and repetition frequency of the pulse laser light L emitted from the laser light source 11. An example of the wavelength of the pulse laser light L emitted from the laser light source 11 is 5.75 μm. Examples of the pulse width range from 10 ns to 1 ms, while examples of the repetition frequency range from 500 Hz to 2 MHz.

The irradiation optical system 13 may have an optical fiber 14 which can guide the pulse laser light L emitted from the laser light source 11, an entrance lens system 15 for causing the pulse laser light L emitted from the laser light source 11 to enter one end of the optical fiber 14, and a condenser lens system 16 for irradiating the carious tooth 20 with the pulse laser light L emitted from the other end of the optical fiber 14. The irradiation optical system 13 may have any structure, without being restricted to the one using the optical fiber 14, as long as the object to be treated can be irradiated with the laser light L emitted from the laser light source 11. For example, an articulated optical waveguide may be utilized as an optical waveguide for guiding light in the irradiation optical system 13.

The laser light source 11 and irradiation optical system 13 are combined with each other so as to optimize optical conditions such as optical axis adjustment. Verification of irradiation position of the pulse laser light L having a wavelength within the wavelength region of 5.7 to 6.6 μm, and so forth, can be performed in the same way when using a medical carbon dioxide laser having a wavelength of 10.6 μm which has been in medical use.

In the above-mentioned structure, the pulse laser light L having a wavelength within the wavelength region of 5.7 to 6.6 μm emitted from the laser light source 11 driven by the controller 12 enters the optical fiber 14 through the entrance lens system 15. The pulse laser light L having entered the optical fiber 14 propagates therethrough and exits from the other end thereof. The pulse laser light L emitted from the other end of the optical fiber 14 is converged by the condenser lens system 16, so as to irradiate the carious part 21 of the carious tooth 20. A dentist can irradiate the carious part 21 with the pulse laser light L by operating the irradiation optical system 13 while observing the carious tooth 20.

By using the pulse laser light L having a wavelength within the above-mentioned wavelength region, the dental therapy apparatus 10A can confine its treatment area to the carious part 21, which is a part to be treated (lesion tissue), as illustrated in Experimental Example 1 which will be explained later. Such a spatial restriction on an interaction area seems to be attributable to the difference in hardness between the carious part 21 and a sound part 22 not infected with cariogenic bacteria. Here, wavelengths (in the band of 9 to 10 μm) absorbed by the sound part 22 from the carious part 21 cannot be utilized. A biological tissue has a characteristic absorption pattern derived from molecular vibrations in a mid-infrared wavelength region; in particular, wavelengths corresponding to amides I and II (having center wavelengths of 6.1 μm and 6.45 μm, respectively, in their absorption bands) which are absorption bands derived from amide bonds of proteins are strongly absorbed by soft biological tissues. In caries, cariogenic bacteria seem to alter properties of the carious site 21 from those of the sound part 22, thereby making it easier for the absorption to cause a cutting reaction. Therefore, utilizing the pulse laser light L emitted from the laser light source 11 can cut the carious part 21 while making it less influential on the sound part 22.

Controlling the pulse state of the pulse laser light L can regulate temporal interactions between the pulse laser light L and the area irradiated therewith. In the dental therapy apparatus 10A, the controller 12 controls the pulse width and repetition frequency of the pulse laser light L emitted from the laser light source 11. Hence, controlling the pulse width and repetition frequency can adjust cutting conditions, an example of which is the cutting speed.

As mentioned above, the dental therapy apparatus 10A can control the pulse laser light L and its irradiation area spatially and temporally, thereby enabling minimally invasive treatment. Even when located near a soft tissue such as a gum G (see FIG. 1), the carious part 21 can be treated without damaging the soft tissue, if the cutting speed is adjusted by controlling a pulse state such as the pulse width of the pulse laser light while observing the carious part 21.

The mid-infrared light having a wavelength within the wavelength region of 5.7 to 6.6 μm exerts a thermal action on biological tissues. This thermal action can be adjusted by controlling the pulse width (interaction time) and repetition frequency.

In the thermal action, thermal relaxation time is important. For example, the thermal relaxation time of biological tissues with respect to laser light within the wavelength region of 5.7 to 6.6 µm is on the order of µs. Hence, irradiation with the pulse laser light L having a pulse width on the order of ns (up to about 10 µs) and a repetition frequency of about 1 to 1000 Hz can cut the carious part 21 while depressing the thermal effect.

On the other hand, the pulse laser light L having a pulse width on the order of µs to ms and a repetition frequency of 1000 Hz or higher can provide its irradiation area with a strong interaction of the thermal effect suitable for melting/coagulating. Specifically, light having a wavelength within the wavelength region of 5.7 to 6.6 µm is efficiently absorbed by proteins and thus can ablate the soft tissue. Under conditions satisfying a longer pulse width and shorter pulse interval than the thermal relaxation time of the irradiation area of the pulse laser light L, heat diffuses to the outside of the irradiation region. When the temperature reaches 60° C. or higher due to the heating effect caused by the diffusion, the soft tissue can coagulate. The coagulation of the soft tissue about the cut part can clog blood vessels and bring about a hemostatic effect. This can also be understood from a comparison with carbon dioxide lasers in medical use. That is, when absorption characteristics of biological tissues are taken into consideration, the absorption coefficient at a wavelength of 5.75 µm within the wavelength region of 5.7 to 6.6 µm, for example, is about 500 $cm^{-1}$. This value is substantially the same as the absorption coefficient (about 600 $cm^{-1}$) of carbon dioxide lasers in medical use at a wavelength of 10.6 µm. The blood clotting and stanching capability of carbon dioxide lasers has been utilized in various medical departments. Hence, light (e.g., with a wavelength of 5.75 µm) having an absorption characteristic similar to that of carbon dioxide lasers can cut soft tissues and clot and stanch blood as mentioned above.

In view of the foregoing, the dental therapy apparatus 10A having the controller 12 as a mechanism adapted to change the pulse width and repetition frequency is applicable not only to cutting the carious part 21 of the carious tooth 20, but also to ablating soft tissues, stanching blood, and so forth. Since the dental therapy apparatus 10A can also stop bleeding, increasing the repetition frequency of the pulse laser light L can stanch blood even if a soft tissue is damaged to bleed. Therefore, the dental therapy apparatus 10A can attain optimal therapeutic effects.

The dental therapy apparatus 10A by itself can stanch blood and so forth while cutting the carious part 21, whereby no other apparatus are necessary for stanching blood and so forth. Hence, dentists can treat teeth while effectively utilizing treatment room spaces.

The quantum cascade laser has a cascade structure in which light-emitting layers are connected in multiple stages and thus can emit light with higher power. Therefore, employing the quantum cascade laser can cut the carious part 21 and the like more surely. Since the quantum cascade laser emits light having a wavelength in the wavelength region of 5.7 to 6.6 µm by utilizing intersubband transitions in a quantum well structure, the laser light source 11 is smaller than those based on difference-frequency generation, for example. Hence, as mentioned above, dentists can treat teeth by effectively utilizing treatment room spaces.

Operations and effects of the dental therapy apparatus 10A will now be explained more specifically according to experiment results. While experimental conditions such as wavelength and pulse state will be illustrated for explaining experiments, the present invention is not limited to the wavelength, pulse condition, and the like set forth in the following.

Figure 2:
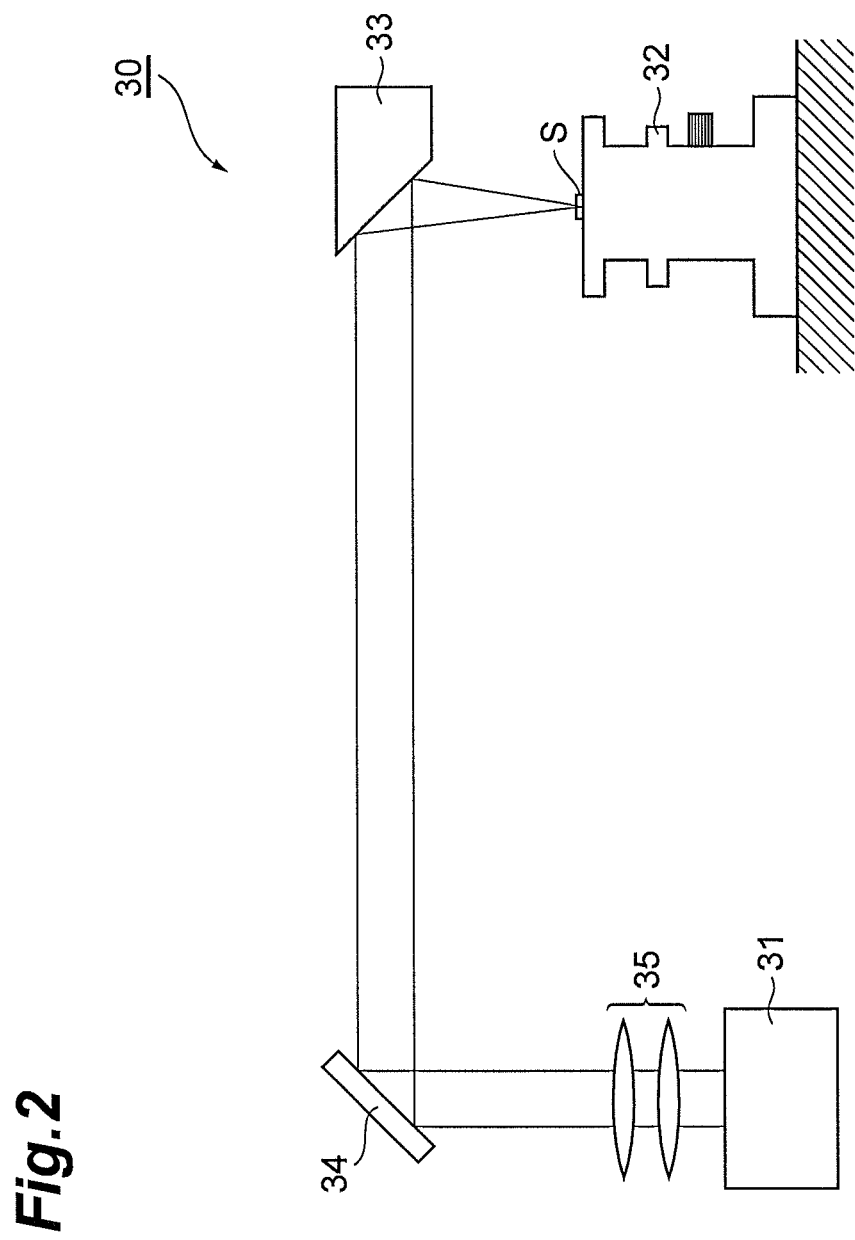
FIG. 2 is a schematic view illustrating a general structure of an experimental apparatus.

First, an experimental apparatus will be explained with reference to FIG. 2. FIG. 2 is a schematic view illustrating a general structure of the experimental apparatus.

This experimental apparatus 30 has a light source unit 31 that emits laser light, a three-dimensional stage 32 on which a sample S is mounted, a parabolic mirror 33 that converges the laser light emitted from the light source unit 31 onto the sample S mounted on the three-dimensional stage 32, a plane mirror 34 that reflects the laser light emitted from the light source unit 31 toward the parabolic mirror 33, and an attenuator 35, arranged between the light source unit 31 and the plane mirror 34, that adjusts the quantity of laser light. The parabolic mirror 33 has a focal length of about 5 cm. Experimental Examples 1 to 4 utilizing the experimental apparatus 30 will be explained.

Experimental Example 1

In Experimental Example 1, a sound dentin of a bovine tooth and a decalcified dentin obtained by treating a bovine dentin with an aqueous lactic acid solution were prepared as sound and carious tooth samples S1, S2, respectively. Each of the sound and carious tooth samples S1, S2 was set as the sample S on the three-dimensional stage 32. The light source unit 31 of Experimental Example 1 was a DFG laser having the same structure as that described in Non Patent Literature 1.

In Experimental Example 1, laser light having predetermined wavelengths within the wavelength region of 5.70 to 6.55 µm was emitted from the light source unit 31. The predetermined wavelengths are in increments of 0.05 µm within the above-mentioned wavelength region. Irradiation conditions are as follows:

Pulse width: 5 ns
Repetition frequency: 10 Hz
Average power density: 20 $W/cm^2$
Irradiation time: 1 sec Irradiation marks of the sound and carious tooth samples S1, S2 irradiated with the pulse laser light were observed with a scanning microscope. FIG. 3 is a chart illustrating how the sound and carious tooth samples S1, S2 are cut at wavelengths in increments of 0.05 µm within the wavelength region of 5.70 to 6.55 µm.

As illustrated in FIG. 3, the carious tooth sample S2 is cut by a greater amount than the sound tooth sample S1 in the experimental wavelength region. Hence, the laser light having a wavelength within the wavelength region of 5.70 to 6.55 µm is less invasive to sound parts (or sound teeth) and can selectively treat carious parts (carious teeth). In particular, it is understandable that the laser light having a wavelength ranging from 5.75 to 5.85 µm is excellent in minimal invasiveness to sound parts.

Experimental Example 2

As with Experimental Example 1, the sound and carious tooth samples S1, S2 were prepared. In Experimental Example 2, the light source unit 31 comprises a quantum cascade laser that emits laser light having a wavelength of 5.75 µm and a controller therefor. In this case, the experimental apparatus 30 of Experimental Example 2 corresponds to the dental therapy apparatus 10A including the plane mirror 34 and parabolic mirror 33 as the irradiation optical system 13.

In Experimental Example 2, each of the sound and carious tooth samples S1, S2 was mounted as the sample S on the three-dimensional stage 32 and was irradiated with the pulse laser light emitted from the light source unit 31. Pulse laser light irradiation conditions are as follows:
Pulse width: 500 ns
Repetition frequency: 1 kHz
Average power density: 500 W/cm$^2$
Irradiation time: 2 sec Irradiation marks of the sound and carious tooth samples S1, S2 irradiated with the pulse laser light were observed with the scanning microscope.

FIG. 4(a) is a picture illustrating the irradiation mark of the sound tooth sample. FIG. 4(b) is a picture illustrating the irradiation mark of the carious tooth sample. It is observed from FIGS. 4(a) and 4(b) that the carious tooth sample S2 is cut by a greater amount than the sound tooth sample S1. No cracks are seen on the surface of the sound tooth sample S1 where no cuts are observed. These make it understandable that the quantum cascade laser adapted to emit laser light having a wavelength of 5.75 μm is less invasive to sound parts (or sound teeth) and can selectively treat carious parts (carious teeth).

Experimental Example 3

In Experimental Example 3, a two-tiered sample S4 in which a carious sample part obtained by treating a bovine dentin with an aqueous lactic acid solution was disposed on a sound tooth sample part was prepared. The two-tiered sample S4 was irradiated with the pulse laser light from the light source unit 31 under the same condition as with Experimental Example 2 except that the sample was changed to the two-tiered sample S4. The two-tiered sample S4 was irradiated with the pulse laser light from the carious tooth sample part side. After the irradiation with the pulse laser light, a cross section of an irradiation mark was observed with an optical microscope.

Figure 5:
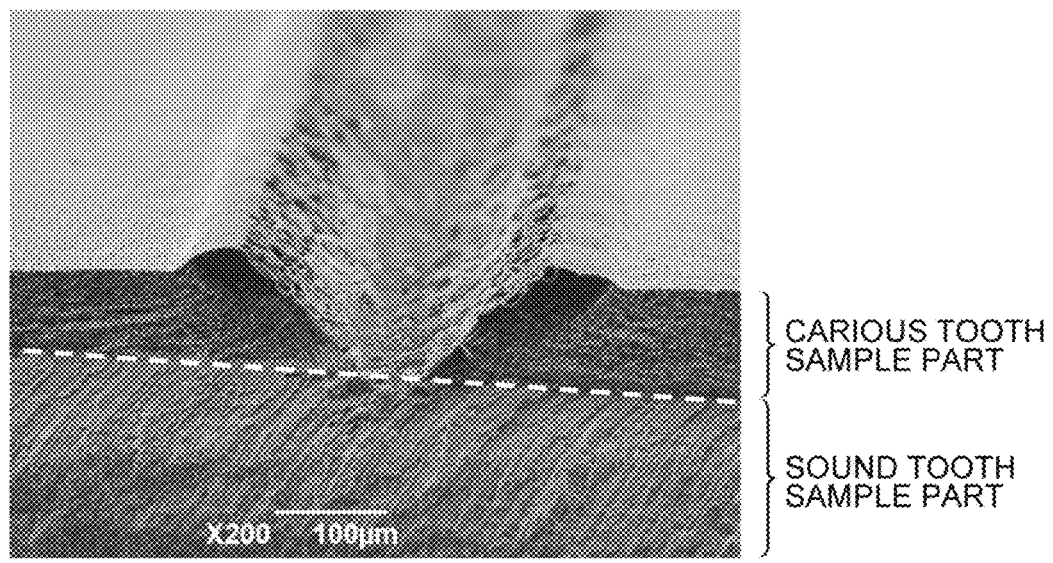
FIG. 5 is a picture illustrating an experiment result of irradiating a two-tiered sample with laser light.

FIG. 5 is a picture illustrating the irradiation mark cross section. The broken line in FIG. 5 indicates the boundary between the carious and sound parts. FIG. 5 makes it understandable that cutting stops at the boundary between the carious and sound parts. This demonstrates that the laser light having a wavelength of 5.75 μm does not react with sound parts but carious parts.

Experimental Example 4

In Experimental Example 4, chicken breast was prepared as a soft biological tissue S5 and the soft biological tissue S5 was mounted on the three-dimensional stage 32. Then, as in Experimental Examples 2 and 3, the soft biological tissue S5 was irradiated with the pulse laser light having a wavelength of 5.75 μm emitted from the light source unit 31 including the quantum cascade laser. Irradiation conditions are as follows:
Pulse width: 500 ns
Repetition frequency: 1 kHz
Average power density: 2500 W/cm$^2$
Irradiation time: 5 sec Next, the light source unit 31 was changed to a medical carbon dioxide laser apparatus (Lezawin CH S manufactured by J. Morita Manufacturing Corporation), laser light having a wavelength of 10.6 μm was emitted from the light source unit 31, and the soft biological tissue S5 was irradiated with the laser light as a continuous wave (CW). Irradiation conditions are as follows:
Average power density: 2500 W/cm$^2$
Irradiation time: 5 sec Each of respective irradiation mark cross sections of the soft biological tissue samples S5 irradiated with the laser light having a wavelength of 5.75 μm emitted from the quantum cascade laser and the laser light having a wavelength of 10.6 μm emitted from the medical carbon dioxide laser apparatus was observed under hematoxylin-eosin stain, which is a typical histological evaluation technique.

FIG. 6(a) is a picture illustrating the irradiation mark cross section of the sample irradiated with the laser light having a wavelength of 5.75 μm, while FIG. 6(b) is a picture illustrating the irradiation mark cross section of the sample irradiated with the laser light having a wavelength of 10.6 μm.

When FIGS. 6(a) and 6(b) are compared with each other, the incising action in the case of using the quantum cascade laser is similar to that in the case of using the medical carbon dioxide laser. Coagulation and carbonization are generated in both of FIGS. 6(a) and 6(b), but to a lesser extent in FIG. 6(a). Therefore, the structure of the laser light source 11 illustrated in FIG. 1 may be clinically superior from the viewpoint of yielding appropriate coagulation and no excessive carbonization. The difference in coagulation/carbonization seems to be attributable to the pulse structure, i.e., a short pulse with a high repetition frequency, in the quantum cascade laser. Since the mechanism (controller 12) adapted to change the pulse width and repetition frequency can control the balance between the incising action and the blood clotting and stanching action, the dental therapy apparatus 10A comprising the laser light source 11 and controller 12 illustrated in FIG. 1 can perform sophisticated cutting of soft tissues.

Figure 7:
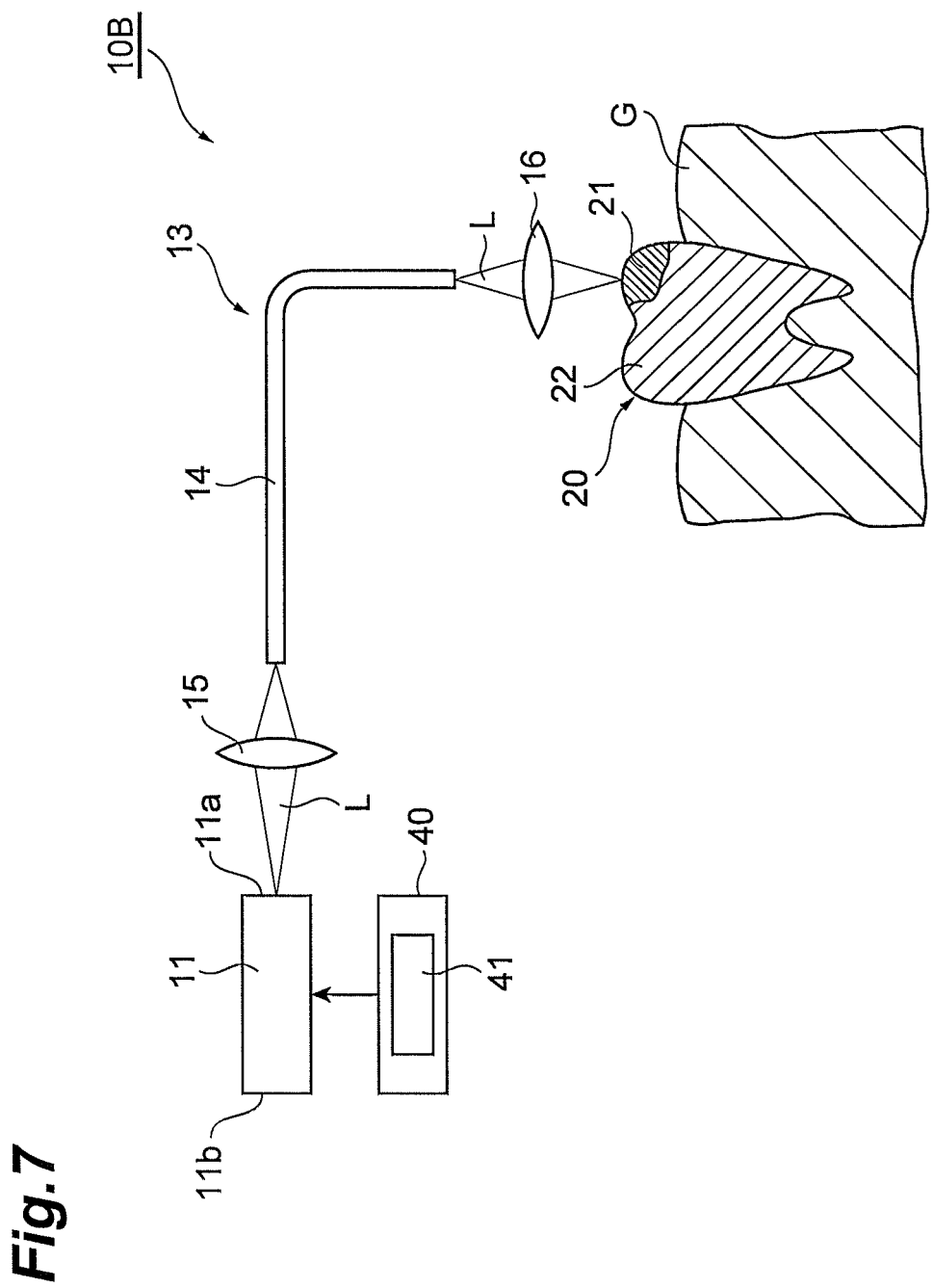
FIG. 7 is a schematic view illustrating a general structure of an example of dental therapy apparatus in accordance with another embodiment.

FIG. 7 is a schematic view illustrating a general structure of the dental therapy apparatus in accordance with another embodiment. The dental therapy apparatus 10B illustrated in FIG. 7 differs from the dental therapy apparatus 10A illustrated in FIG. 1 in that the controller 40 is equipped with a mode switcher 41. The constituents other than the controller 40 are the same as those in FIG. 1 and thus will not be explained.

The mode switcher 41 in the controller 40 switches the pulse state of the pulse laser light L having a predetermined wavelength (e.g., 5.75 μm) emitted from the laser light source 11 between a cutting mode (first mode) and a blood stanching mode (second mode). Specifically, in the cutting mode, the controller 40 drives the laser light source 11, which is a quantum cascade laser, at such a pulse width and repetition frequency that the carious part 21 can be cut. In the blood stanching mode, the controller 40 drives the laser light source 11, which is a quantum cascade laser, at such a pulse width and repetition frequency that soft tissues can stop bleeding.

The pulse width and repetition frequency in each of the cutting and blood stanching modes are defined according to the thermal relaxation time of the area irradiated with the pulse laser light L. Specifically, in the cutting mode, the controller 40 drives the laser light source 11 at a pulse width shorter than the thermal relaxation time and a repetition frequency lower than that corresponding to the thermal relaxation time. In the blood stanching mode, the controller 40 drives the laser light source 11 at a pulse width longer than the thermal relaxation time and a repetition frequency higher than that corresponding to the thermal relaxation time. For instance, when the thermal relaxation time of an organism with respect to light in the wavelength region of 5.7 to 6.6 μm is on the order of μs, respective examples of the pulse width and repetition frequency for cutting are 5 ns to 1 μs and 1 Hz to 1 kHz. On the other hand, when the thermal relaxation time of an organism with respect to light in the wavelength region of 5.7 to 6.6 μm is on the order of μs, respective examples of the pulse width and repetition frequency for stanching blood are 1 μs or longer and 1 kHz or higher or may have a duty cycle of 50% or greater.

The dental therapy apparatus 10B, which has the same structure as with the dental therapy apparatus 10A except that the controller 40 is equipped with the mode switcher 41, can exhibit the same operations and effects as with the dental therapy apparatus 10A. Since the mode switcher 41 in the controller 40 can switch between the cutting mode and blood stanching mode, the cutting and stanching blood can easily be changed over from one to the other. Therefore, even if a soft tissue (e.g., gum G) about the carious part 21 bleeds during cutting in the cutting mode or the like, blood stanching treatment can be performed more surely and more rapidly.

Without being restricted to the embodiments of the present invention explained in the foregoing, the present invention can be modified in various ways within the scope not deviating from the gist of the invention.

For example, the laser light source is not limited to the quantum cascade laser, but may be any light source as long as it can emit laser light having a wavelength within the wavelength region of 5.70 to 6.60 μm while its pulse width and repetition frequency can be controlled by the controller. The controller is assumed to control the pulse width and repetition frequency, but may control at least one of them.

REFERENCE SIGNS LIST 10A, 10B . . . dental therapy apparatus; 11 . . . laser light source; 12 . . . controller; 20 . . . tooth having a carious part; 21 . . . carious part; 40 . . . controller; 41 . . . mode switcher

The invention claimed is:

1. A dental therapy apparatus comprising:
a laser light source emitting laser light having a wavelength within a wavelength region of 5.7 to 6.6 μm, the laser light source being a quantum cascade laser;
a controller pulse-driving the laser light source and controlling at least one of pulse width and repetition frequency of pulsed laser light emitted from the laser light source, wherein the controller switches the control of the laser light source between a first mode of driving the laser light source at a pulse width shorter than a thermal relaxation time of an area irradiated with the pulsed laser light and a repetition frequency lower than that corresponding to the thermal relaxation time and a second mode of driving the laser light source at a pulse width longer than the thermal relaxation time and a repetition frequency higher than that corresponding to the thermal relaxation time, wherein the repetition frequency for the first mode is 1 Hz to 1 kHz and the repetition frequency for the second mode is at least 1 kHz, and wherein the pulse width for cutting in the first mode is 5 ns to 1 μs and the pulse width for the second mode is at least 1 μs; and
an irradiation optical system for irradiating a tooth including a carious part with the light emitted from the laser light source;
wherein the controller controls at least one of the pulse width and repetition frequency of the pulsed laser light, so as to selectively cut the carious part included in the tooth.

* * * * *